United States Patent
Menovcik et al.

(10) Patent No.: US 8,076,425 B2
(45) Date of Patent: Dec. 13, 2011

(54) CARBAMATE FUNCTIONAL SILICA COMPOUNDS AND METHODS OF MAKING AND USE THEREOF

(75) Inventors: Gregory G. Menovcik, Northville, MI (US); Walter H. Ohrbom, Hartland Township, MI (US)

(73) Assignee: BASF Coatings GmbH, Muenster (DE)

(*) Notice: Subject to any disclaimer, the term of this patent is extended or adjusted under 35 U.S.C. 154(b) by 1626 days.

(21) Appl. No.: 11/239,606

(22) Filed: Sep. 29, 2005

(65) Prior Publication Data
US 2007/0232776 A1    Oct. 4, 2007

Related U.S. Application Data

(60) Provisional application No. 60/615,417, filed on Oct. 1, 2004.

(51) Int. Cl.
| | |
|---|---|
| C08F 283/00 | (2006.01) |
| C08F 283/12 | (2006.01) |
| C08G 77/00 | (2006.01) |
| C08G 77/38 | (2006.01) |
| C08G 73/00 | (2006.01) |
| C08L 83/00 | (2006.01) |
| C08F 6/22 | (2006.01) |
| C01B 33/12 | (2006.01) |

(52) U.S. Cl. ......... 525/474; 528/422; 528/492; 423/335
(58) Field of Classification Search .................. 528/128, 528/422, 492; 423/335; 525/474
See application file for complete search history.

(56) References Cited

U.S. PATENT DOCUMENTS

| | | | |
|---|---|---|---|
| 3,906,018 A | 9/1975 | Ostrozynski | |
| 4,496,754 A * | 1/1985 | Kanner et al. | 556/420 |
| 4,677,004 A * | 6/1987 | Das et al. | 427/407.1 |
| 4,954,327 A * | 9/1990 | Blount | 423/338 |
| 5,853,809 A * | 12/1998 | Campbell et al. | 427/407.1 |
| 5,939,491 A | 8/1999 | Wilt et al. | |
| 5,976,701 A * | 11/1999 | Barancyk et al. | 428/423.1 |
| 5,977,220 A * | 11/1999 | Burkus et al. | 524/99 |
| 6,013,643 A * | 1/2000 | Sakamoto et al. | 514/188 |
| 6,040,394 A | 3/2000 | Wilt et al. | |
| 6,046,276 A | 4/2000 | Ambrose et al. | |
| 6,046,296 A | 4/2000 | Wilt et al. | |
| 6,048,934 A | 4/2000 | Wilt et al. | |
| 6,069,221 A | 5/2000 | Chasser et al. | |
| 6,103,824 A | 8/2000 | Wilt et al. | |
| 6,103,838 A | 8/2000 | Wilt et al. | |
| 6,136,928 A | 10/2000 | Wilt et al. | |
| 6,187,863 B1 | 2/2001 | Wilt et al. | |
| 6,225,434 B1 | 5/2001 | Sadvary et al. | |
| 6,274,672 B1 | 8/2001 | Ambrose et al. | |
| 6,376,607 B1 | 4/2002 | Ambrose et al. | |
| 6,387,519 B1 * | 5/2002 | Anderson et al. | 428/447 |
| 6,534,188 B2 | 3/2003 | Sadvary et al. | |
| 6,541,119 B2 | 4/2003 | Sadvary et al. | |
| 6,593,417 B1 | 7/2003 | Anderson et al. | |
| 6,610,777 B1 | 8/2003 | Anderson et al. | |
| 6,623,791 B2 * | 9/2003 | Sadvary et al. | 427/140 |
| 6,635,341 B1 | 10/2003 | Barancyk et al. | |
| 6,657,001 B1 | 12/2003 | Anderson et al. | |
| 6,673,273 B2 * | 1/2004 | Ba Le et al. | 252/511 |
| 6,759,478 B2 | 7/2004 | Anderson et al. | |
| 6,790,904 B2 | 9/2004 | White et al. | |
| 6,803,408 B2 | 10/2004 | Anderson et al. | |
| 6,987,144 B2 | 1/2006 | Anderson et al. | |
| 7,005,472 B2 | 2/2006 | Anderson et al. | |
| 7,053,149 B2 | 5/2006 | Anderson et al. | |
| 7,151,122 B2 | 12/2006 | DeSaw et al. | |
| 7,172,809 B2 | 2/2007 | Barancyk et al. | |
| 2002/0119253 A1 * | 8/2002 | Ohrbom et al. | 427/384 |
| 2002/0128336 A1 * | 9/2002 | Kolb et al. | 521/50 |
| 2002/0136901 A1 * | 9/2002 | Ramesh et al. | 428/423.1 |
| 2002/0155278 A1 * | 10/2002 | Boisseau et al. | 428/331 |

(Continued)

FOREIGN PATENT DOCUMENTS

DE     2323397     11/1973

(Continued)

OTHER PUBLICATIONS

XP-002361083, K.S. Anisia, A. Kumar, 20 Feb. 20, 2004.

(Continued)

*Primary Examiner* — Liam Heincer
(74) *Attorney, Agent, or Firm* — Harness, Dickey & Pierce, P.L.C.

(57) ABSTRACT

Disclosed is a carbamate functional silica, comprising repeating units:

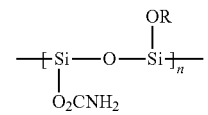

wherein R is H or an alkyl group of from 1 to 50 carbon atoms and n is a number from 1 to 100. Also disclosed is a functional silica comprising repeating units:

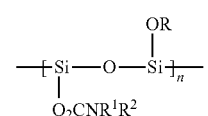

wherein R is an alkyl group of from 1 to 50 carbon atoms, n is from 1 to 100, $R^1$ and $R^2$ may be the same or different and are at least one of a hydrocarbon group comprising from 1 to 100 carbon atoms with the proviso that at least one of $R^1$ and $R^2$ is not hydrogen. In one embodiment, $R^1$ and $R^2$ are hydrogen or the residual of an aminoplast polymer, an alkylating alcohol, or the like. Methods for making the disclosed functional silicas and coating compositions comprising the same are also provided.

10 Claims, No Drawings

U.S. PATENT DOCUMENTS

| | | | |
|---|---|---|---|
| 2003/0050498 A1* | 3/2003 | Bammel et al. | 560/24 |
| 2004/0185269 A1* | 9/2004 | Loper et al. | 428/447 |
| 2004/0236034 A1* | 11/2004 | Ohrbom et al. | 525/418 |
| 2005/0003114 A1* | 1/2005 | Nakano et al. | 428/32.34 |
| 2005/0054848 A1* | 3/2005 | Valta et al. | 536/32 |
| 2005/0131134 A1* | 6/2005 | Green et al. | 524/589 |
| 2005/0182231 A1* | 8/2005 | Green et al. | 528/272 |
| 2005/0182232 A1* | 8/2005 | Ramesh et al. | 528/272 |
| 2006/0030663 A1* | 2/2006 | Andre et al. | 524/588 |

FOREIGN PATENT DOCUMENTS

| | | |
|---|---|---|
| EP | 0832947 | 4/1998 |
| GB | 1110331 | 5/1965 |

OTHER PUBLICATIONS

XP-001233525, Deeptangshu S. Chaudhary, Aug. 2, 2002.

XP-002361085, English Abstract.

* cited by examiner

CARBAMATE FUNCTIONAL SILICA COMPOUNDS AND METHODS OF MAKING AND USE THEREOF

CROSS REFERENCE TO RELATED APPLICATION

This application is a non-provisional of U.S. Ser. No. 60/615,417 filed on 1 Oct. 2004, which is incorporation herein by reference.

FIELD OF THE INVENTION

The invention relates to curable coating compositions, especially thermoset curable coating compositions for use on automotive exterior panels.

BACKGROUND OF THE INVENTION

Curable coating compositions, especially thermoset coatings, are widely used in the coatings art. They are often used for topcoats in the automotive and industrial coatings industry.

High-gloss and color-plus-clear composite coatings are particularly useful as topcoats where exceptional gloss, depth of color, distinctness of image, or special metallic effects are desired. The automotive industry has made extensive use of these coatings for automotive body panels. These coatings require an extremely high degree of clarity and a low degree of visual aberrations at the surface of the coating in order to achieve desired visual effects such as a high distinctness of image (DOI).

As a result, high-gloss and composite color-plus-clear coatings are susceptible to a phenomenon known as environmental etch. Environmental etch manifests itself as spots or marks on or in the finish of the coating that often cannot be rubbed out. It can be difficult to predict the degree of resistance to environmental etch that a high gloss or color-plus-clear composite coating will exhibit. Many coating compositions known for their durability and/or weatherability when used in exterior paints, such as high-solids enamels, do not provide the desired level of resistance to environmental etch when used in high gloss coatings and color-plus-clear composite coatings.

Many compositions have been proposed for use as the clearcoat portion of color-plus-clear composite coating systems, such as polyurethanes, acid-epoxy systems and the like. However, many prior art systems suffer from disadvantages such as coatability problems, compatibility problems with the pigmented basecoat, and/or solubility problems. Moreover, very few one-pack coating compositions have been found that provide satisfactory resistance to environmental etch, especially in the demanding environment of automotive coatings.

It has been found that carbamate functional polymers such as those described in U.S. Pat. No. 5,356,669 can be used to provide coating compositions which exhibit significantly improved environmental etch resistance. Carbamate functional polymers have been used to provide commercially advantageous coatings compositions, especially as clearcoats in composite color-plus-clear coatings.

However, continual improvements in clearcoat coating compositions are always desirable. In particular, it would be advantageous to provide improvements with respect to environmental fallout, exposure to ultraviolet radiation emitted from sunlight, exposure to high relative humidity at high temperature, defects made by small, hard objects resulting in scratching and chipping, scratch and mar resistance, durability, and the like.

Balancing the competing needs of such performance characteristics continues to be challenging, especially with respect to automotive exterior coatings. For example, a harder film may provide a clearcoat that is more resistant to environmental etch, while resulting in a film that is less scratch resistant. A softer film may provide a more scratch resistant coating, with lessened etch resistance. Thus, an optimum balance of performance characteristics with respect to ever changing environmental factors is desirable.

SUMMARY OF THE INVENTION

Disclosed is a carbamate functional silica, comprising repeating units of the structure:

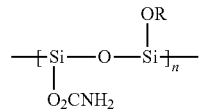

wherein R is hydrogen or a hydrocarbon group of from 1 to 50 carbon atoms and n is a number from 1 to 100. In one exemplary embodiment, the repeating units modify the surface of fumed silica.

Also provided is a method of making the disclosed carbamate functional silica. The disclosed method comprises providing a fumed silica having a plurality of silanol groups, reacting one or more of the silanol groups with at least one of (i) ammonia and hydrogencyanate; (ii) an alkyl carbamate in the presence of a tin catalyst; or (iii) phosgene and ammonia; to provide a carbamate functional silica of the structure:

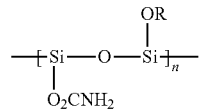

wherein R is hydrogen or a hydrocarbon group of from 1 to 50 carbon atoms and n is a number from 1 to 100.

The disclosed carbamate functional silica may be used to make other functional silicas. In one embodiment, the functional silicas will be useful as crosslinking agents, especially crosslinking agents for powder or particulate compositions.

In one embodiment, a disclosed functional silica comprises repeating units of the structure:

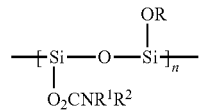

wherein R is hydrogen or an alkyl group of from 1 to 50 carbon atoms, n is a number from 1 to 100, $R^1$ and $R^2$ may be the same or different and are at least one of a hydrocarbon group comprising from 1 to 100 carbon atoms with the proviso that at least one of $R^1$ and $R^2$ is not hydrogen. In one embodiment, $R^1$ and $R^2$ are hydrogen or the residual of an aminoplast polymer, an alkylating alcohol, or the like.

The disclosed functional silicas and crosslinking agents may be used in curable coating compositions, especially clearcoat coating compositions and/or powder coating compositions.

DETAILED DESCRIPTION OF THE PREFERRED EMBODIMENTS

The following description of the preferred embodiment(s) is merely exemplary in nature and is in no way intended to limit the invention, its application, or uses.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates a possible variation of up to 5% in the value.

In one embodiment, a carbamate functional silica is disclosed, comprising repeating units of the structure (I):

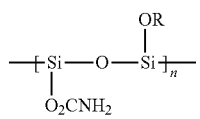

wherein R is hydrogen or a hydrocarbon group of from about 1 to 50 carbon atoms and n is a number from about 1 to 100. In one exemplary embodiment, the repeating units modify the surface of fumed silica, providing improved fumed silica having a carbamate functionality attached to its surface that is useful in coating compositions.

In one embodiment, various repeating units will have different R's, that is, on any particular fumed silica, there may be both silanol groups, i.e., —SiOH groups, as well as siloxy groups —SiOR, as well as the disclosed carbamate functionality —OC(O)NH$_2$.

In one embodiment, R will be a hydrocarbon group that may be an alkyl group, an aryl group, a cycloaliphatic group, or a heteroatom containing group, or a mixture thereof. In one exemplary embodiment, R will be an alkyl group of from 1 to 50 carbons, while in another embodiment, R will be an alkyl group of from 1 to 25 carbon atoms. In one particularly exemplary embodiment, R will be an alkyl group of from 1 to 10 carbon atoms.

The disclosed carbamate functional silica may be made by a disclosed method comprises providing a fumed silica having a plurality of silanol groups, reacting one or more of the silanol groups with at least one of (i) ammonia and hydrogencyanate; (ii) an alkyl carbamate in the presence of a tin catalyst; or (iii) phosgene and ammonia; to provide a carbamate functional silica of the structure:

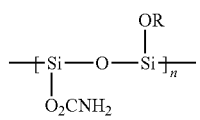

wherein R is hydrogen or a hydrocarbon group of from 1 to 50 carbon atoms and n is a number from 1 to 100.

For example, in one embodiment, the disclosed carbamate functional silicas may be made chemically modifying the silanol groups (—SiOH) present on the surface of fumed silica. Such chemical modification comprises exposing a suitable fumed silica to reactants that are reactive with the silanol hydroxyl group and that are either carbamate functional or comprise a group convertible to a carbamate group.

In one embodiment suitable fumed silicas are those commercially available and generally characterized by a chain-like particulate structure having a high surface area per unit weight. In one embodiment, a suitable fumed silica may have the following characteristics: a surface area of from 50 to 400 m$^2$/g, a bulk density of from 2.3 to 10.0 lbs/ft$^3$, a loss on ignition of from 0.5 to 2.5 (max % at 1000° C.), and a silica content of greater than 99.9 (% SiO$_2$ dry basis). The evaluation of such characteristics generally assumes a spherical particle and is determined from BET surface area.

The production of fumed silica is a well-documented process which involves the hydrolysis of silicon tetrachloride vapor in a flame of hydrogen and oxygen. Molten spheres of silica are formed in the combustion process, the diameters of the spheres being varied through process parameters and averaging about 7 to 40 millimicrons. These molten spheres of fumed silica, sometimes referred to as primary particles, fuse with one another to form three dimensional branched, chain-like aggregates of approximately 0.1 to 0.5 micron in length. Cooling takes place very quickly, limiting the growth and ensuring that the fumed silica is amorphous. These aggregates in turn form agglomerates ranging and size from 0.5 to 44 microns (325 Mesh).

In one embodiment, suitable fumed silicas will have a surface area between 50 m.sup.2/g and 400 m.sup.2/g (as measured by the nitrogen adsorption method of S. Brunauer, P. H. Emmet and I. Teller, J. Am. Chemical Society, vol. 60, page 309 (1938)). Although many commercially available fumed silicas are suitable, a most preferred fumed silica is that available under the name of CAB-O-SIL™ and having a surface area of about 200 m.sup.2/g. (CAB-O-SIL™ is a registered trademark of Cabot Corporation.) Such a silica has been found to be of high quality and readily dispersable.

In one embodiment, suitable fumed silica may also comprise surface modifying treatments. Examples of such surface modifications include surfactants and silane coupling agents, such as RSi(OMe)$_3$ that are used to improve the adhesion of polymers to a silanol-terminated surface.

In one embodiment, the chemical modification of the silanol groups of a suitable fumed silica will be done by exposing a suitable fumed silica to urea under reactions conditions that cause the urea to decompose.

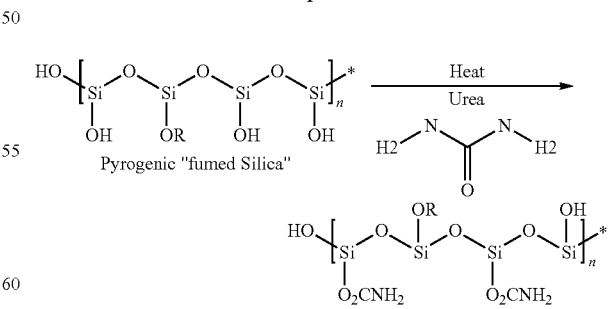

The decomposition of the urea results in the generation of ammonia and hydrogencyanate (HNCO) that results in the formulation of primary carbamate groups.

In another embodiment, the chemical modification of the silanol groups of a suitable fumed silica will be done by exposing a suitable fumed silica to an alkyl carbamate in the presence of heat and suitable transesterification catalysts.

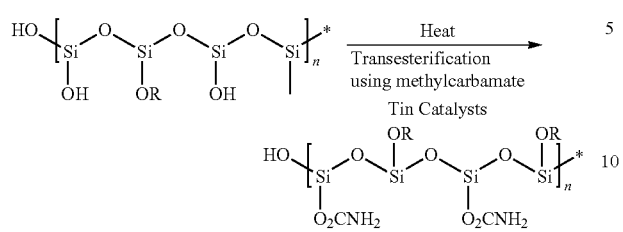

Suitable alkyl carbamate include those having alkyl groups of from 1 to 10 carbon atoms, while in one embodiment, suitable alkyl carbamates will be those having alkyl groups of from 1 to 5 carbon atoms. In one exemplary embodiment, suitable alkyl carbamate carbamates will be those having alkyl groups of from 1 to 3 carbon atoms. Suitable transesterification catalyst include tin catalysts.

In another embodiment, the chemical modification of the silanol groups of a suitable fumed silica will be done by exposing a suitable fumed silica to phosgene and ammonia.

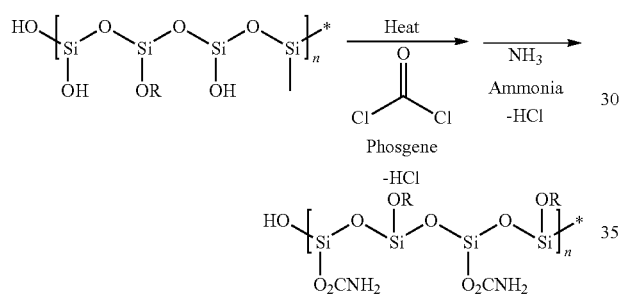

The fumed silica is first exposed to phosgene in the presence of heat and subjected to reaction conditions such that hydrochloric acid is removed as it is generated. Subsequently, the phosgene treated fumed silica is subjected to ammonia and the removal of hydrochloric acid to provide the desired carbamate functional silica.

The reactive primary carbamate group of the disclosed carbamate functional silica may undergo additional reaction. Such reactions may generally provide a functional silica comprising repeating units of the structure (II):

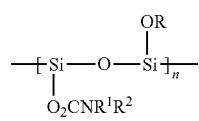

wherein R is H or a hydrocarbon group of from 1 to 50 carbon atoms, n is a number from 1 to 100, $R^1$ and $R^2$ may be the same or different and are at least one of a hydrogen atom or a hydrocarbon group comprising from 1 to 100 carbon atoms with the proviso that at least one of $R^1$ and $R^2$ is not hydrogen.

In one embodiment, R will be a hydrocarbon group that may be an alkyl group, an aryl group, a cycloaliphatic group, or a heteroatom containing group, or a mixture thereof. In one exemplary embodiment, R will be an alkyl group of from 1 to 50 carbons, while in another embodiment; R will be an alkyl group of from 1 to 25 carbon atoms. In one particularly exemplary embodiment, R will be an alkyl group of from 1 to 10 carbon atoms.

Suitable $R^1$ and $R^2$ groups may be the same or different and are at least one of a hydrocarbon group comprising from 1 to 100 carbon atoms. Illustrative hydrocarbon carbons may be an alkyl group, an aryl group, a cycloaliphatic group, a heteroatom containing group, a heterocyclic group, or a mixture thereof. In one embodiment, suitable $R^1$ and $R^2$ groups will comprise functional groups such as esters, ethers, amine groups, heterocyclic structures and the like. In one exemplary embodiment, $R^1$ and $R^2$ groups will comprise six membered heterocyclic structures of the formula $C_3N_3$ or alkyl esters of the formula —$CH_2OR$, wherein R is as defined above.

In one embodiment, $R^1$ and $R^2$ may be the same or different and are at least one of the residual of an aminoplast polymer, an alkylating alcohol, hydrogen, and the like, with the proviso that one of $R^1$ and $R^2$ may not be hydrogen.

In one embodiment, the primary carbamate functional silica disclosed herein will be reacted with an aminoplast compound. Suitable aminoplasts include the generally known condensation products of an aldehyde with an amino- or amido-group containing substance examples of which include the reaction products of formaldehyde, acetaldehyde, crotonaldehyde, benzaldehyde and mixtures thereof with urea, melamine or benzoguanimine. Preferred aminoplast resins include the etherified (i.e. alkylated) products obtained from the reaction of alcohols and formaldehyde with urea, melamine, or benzoguanimine. Examples of suitable alcohols for preparation of these etherified products include: methanol, ethanol, propanol, butanol, isobutanol, t-butanol, hexanol, benzylalcohol, cyclohexanol, 3-chloropropanol, and ethoxyethanol.

In one exemplary embodiment, the aminoplast reacted with the disclosed primary carbamate functional silica will comprise the structure (III):

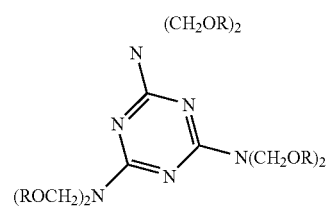

wherein R is as defined above with respect to the functional silica.

In another embodiment, the primary carbamate functional silica disclosed herein will be reacted with an alkylating alcohol in the presence of formaldehyde.

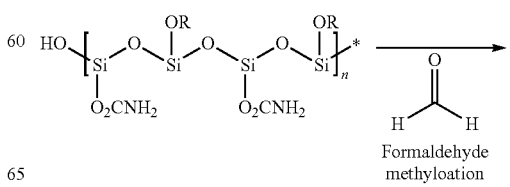

-continued

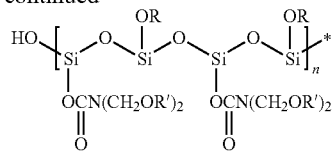

Suitable alkylating alcohols will be of the formula R'OH wherein R' is at least one of —$(CH_2)_xCH_3$ wherein x is a number from 0 to 3. In one exemplary embodiment, R'OH will be methanol.

Thus, in one embodiment, the functional silica may be of the structure (IV) or (V):

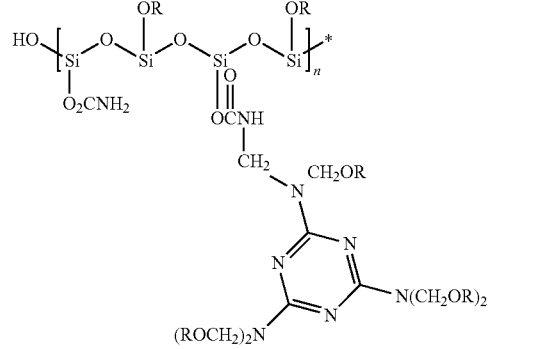

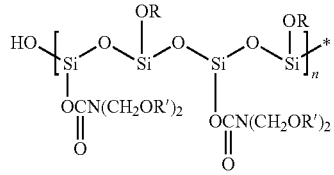

wherein R is may be the same or different with respect to different substituents and is as defined above, and R' is at least one of —$(CH_2)_xCH_3$ wherein x is a number from 0 to 3.

Also provided herein are coating compositions comprising the disclosed functional silicas. In one embodiment, the disclosed functional silicas may be present in a coating composition in an amount of from about 0.1 to 60% by weight, based on total nonvolatile of the coating composition. In another embodiment, the disclosed functional silicas may be present in a coating composition in an amount of from about 5.0 to 40% by weight, based on the total nonvolatile of the coating composition.

In one embodiment, the disclosed coating compositions will also comprise a film-forming component comprising one or more active hydrogen containing compounds, also referred to herein as a crosslinkable resin, and one or more crosslinking agents. For the purposes of clarity, it should be note that although certain substitutents such as R, R', and the like are used both above with respect to the functional silicas and below in connection with the definitions of various crosslinkable resins, each variable has the definition relating to the particularly identified component. That is, the definition of R for the functional silica may be not be used for the definition of R that is associated with a crosslinkable resin.

"Active hydrogen group" as used herein refers to functional groups that donate a hydrogen group during the reaction with the functional groups of the one or more crosslinking agents. Examples of active hydrogen groups are carbamate groups, hydroxyl groups, amino groups, thiol groups, acid groups, hydrazine groups, activated methylene groups, and the like. Preferred active hydrogen groups are carbamate groups, hydroxyl groups, and mixtures thereof.

The crosslinkable resin may be any crosslinkable resin suitable for use in a waterborne, solvent-based, or powder coating composition, especially clearcoat coating compositions.

As used herein, the term "crosslinkable resin" is intended to include not only those resins capable of being crosslinked upon application of heat but also those resins which are capable of being crosslinked without the application of heat. Examples of such crosslinkable resins include thermosetting acrylics, aminoplasts, carbamate functional resins, polyesters, epoxies, silicones and polyamides, modified acrylic polymers, polycarbonates, polyurethanes, polyimides, and polysiloxanes. These resins, when desired, may also contain functional groups characteristic of more than one class, as for example, polyester amides, urethane acrylates, carbamate acrylates, etc. In one embodiment, the crosslinkable resin will be at least one of acrylic polymers, modified acrylics, or polyester polyurethane polymers. In another embodiment, the crosslinkable resin will be an acrylic or polyurethane polymer. In one exemplary embodiment, the crosslinkable resin will be a carbamate functional acrylic.

In one embodiment of the invention, the crosslinkable resin is an acrylic polymer. Suitable acrylic polymers may have a molecular weight of 500 to 1,000,000, and more preferably of 1500 to 50,000. As used herein, "molecular weight" refers to number average molecular weight, which may be determined by the GPC method using a polystyrene standard. Such polymers are well-known in the art, and can be prepared from monomers such as methyl acrylate, acrylic acid, methacrylic acid, methyl methacrylate, butyl methacrylate, cyclohexyl methacrylate, and the like. The active hydrogen functional group, e.g., hydroxyl, can be incorporated into the ester portion of the acrylic monomer. For example, hydroxy-functional acrylic monomers that can be used to form such polymers include hydroxyethyl acrylate, hydroxybutyl acrylate, hydroxybutyl methacrylate, hydroxypropyl acrylate, and the like. Amino-functional acrylic monomers would include t-butylaminoethyl methacrylate and t-butylamino-ethylacrylate. Other acrylic monomers having active hydrogen functional groups in the ester portion of the monomer are also within the skill of the art.

Modified acrylics can also be used as the crosslinkable resin. Such acrylics may be polyester-modified acrylics or polyurethane-modified acrylics, as is well known in the art. Polyester-modified acrylics modified with ∈-caprolactone are described in U.S. Pat. No. 4,546,046 of Etzell et al, the disclosure of which is incorporated herein by reference. Polyurethane-modified acrylics are also well known in the art. They are described, for example, in U.S. Pat. No. 4,584,354, the disclosure of which is incorporated herein by reference.

Preferred carbamate functional acrylics useful as the crosslinkable resin can be prepared in a variety of ways. One way to prepare such polymers is to prepare an acrylic monomer having carbamate functionality in the ester portion of the monomer. Such monomers are well known in the art and are described, for example in U.S. Pat. Nos. 3,479,328, 3,674, 838, 4,126,747, 4,279,833, and 4,340,497, 5,356,669, and WO 94/10211, the disclosures of which are incorporated herein by reference. One method of synthesis involves reaction of a hydroxy ester with urea to form the carbamyloxy carboxylate (i.e., carbamate-modified acrylic). Another method of synthesis reacts an unsaturated acid ester with a hydroxy carbamate ester to form the carbamyloxy carboxylate. Yet another technique involves formation of a hydroxyalkyl carbamate by reacting a primary or secondary amine or diamine with a cyclic carbonate such as ethylene carbonate. The hydroxyl group on the hydroxyalkyl carbamate is then esterified by reaction with acrylic or methacrylic acid to form the monomer. Other methods of preparing carbamate-modified acrylic monomers are described in the art, and can be utilized as well. The acrylic monomer can then be polymerized along with other ethylenically unsaturated monomers, if desired, by techniques well known in the art.

An alternative route for preparing one or more polymers or oligomers useful as the crosslinkable resin is to react an already-formed polymer such as an acrylic polymer with another component to form a carbamate-functional group appended to the polymer backbone, as described in U.S. Pat. No. 4,758,632, the disclosure of which is incorporated herein by reference. Another technique for preparing polymers useful as the crosslinkable resin involves thermally decomposing urea (to give off ammonia and HNCO) in the presence of a hydroxy-functional acrylic polymer to form a carbamate-functional acrylic polymer. Another technique involves reacting the hydroxyl group of a hydroxyalkyl carbamate with the isocyanate group of an isocyanate-functional acrylic or vinyl monomer to form a carbamate-functional acrylic. Isocyanate-functional acrylics are known in the art and are described, for example in U.S. Pat. No. 4,301,257, the disclosure of which is incorporated herein by reference. Isocyanate vinyl monomers are well known in the art and include unsaturated m-tetramethyl xylene isocyanate (sold by American Cyanamid as TMI®). Yet another technique is to react the cyclic carbonate group on a cyclic carbonate-functional acrylic with ammonia in order to form the most preferred carbamate-functional acrylic. Cyclic carbonate-functional acrylic polymers are known in the art and are described, for example, in U.S. Pat. No. 2,979,514, the disclosure of which is incorporated herein by reference. Another technique is to transcarbamylate a hydroxy-functional acrylic polymer with an alkyl carbamate. A more difficult, but feasible way of preparing the polymer would be to trans-esterify an acrylate polymer with a hydroxyalkyl carbamate.

In one embodiment, polymers useful as the crosslinkable resin will generally have a number average molecular weight of 2000-20,000, and preferably from 3000-6000. The carbamate content of the polymer, on a molecular weight per equivalent of carbamate functionality, will generally be between 200 and 1500, and preferably between 300 and 500.

Preferred carbamate functional acrylic crosslinkable resins can be represented by the randomly repeating units according to the following formula:

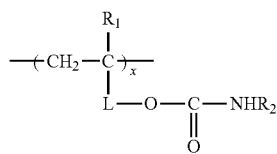

In the above formula, R1 represents H or CH3. R2 represents H, alkyl, preferably of 1 to 6 carbon atoms, or cycloalkyl, preferably up to 6 ring carbon atoms. It is to be understood that the terms alkyl and cycloalkyl are to include substituted alkyl and cycloalkyl, such as halogen-substituted alkyl or cycloalkyl. Substituents that will have an adverse impact on the properties of the cured material, however, are to be avoided. For example, ether linkages are thought to be susceptible to hydrolysis, and should be avoided in locations that would place the ether linkage in the crosslink matrix. The values x and y represent weight percentages, with x being 10 to 90% and preferably 40 to 60%, and y being 90 to 10% and preferably 60 to 40%.

In the formula, A represents repeat units derived from one or more ethylenically unsaturated monomers. As previously discussed, such monomers for copolymerization with acrylic monomers are known in the art. Preferred such monomers will include alkyl esters of acrylic or methacrylic acid, e.g., ethyl acrylate, butyl acrylate, 2-ethylhexyl acrylate, butyl methacrylate, isodecyl methacrylate, hydroxyethyl methacrylate, hydroxypropyl acrylate, and the like; and vinyl monomers such as unsaturated m-tetramethyl xylene isocyanate (sold by American Cyanamid as TMI®), styrene, vinyl toluene and the like.

L represents a divalent linking group, preferably an aliphatic of 1 to 8 carbon atoms, cycloaliphatic, or aromatic linking group of 6 to 10 carbon atoms. Examples of L include

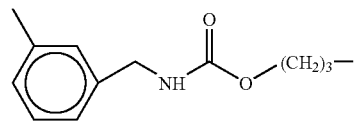

—(CH$_2$)—, —(CH$_2$)$_2$—, —(CH$_2$)$_4$—, and the like. In one preferred embodiment, -L- is represented by —COO-L'- where L' is a divalent linking group. Thus, in one exemplary embodiment, the crosslinkable resin is represented by randomly repeating units according to the following formula:

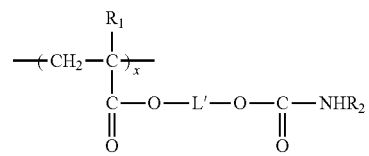

In this formula, R$_1$, R$_2$, A, x, and y are as defined above. L' may be a divalent aliphatic linking group, preferably of 1 to 8 carbon atoms, e.g., —(CH$_2$)—, —(CH$_2$)$_2$—, —(CH$_2$)$_4$—, and the like, or a divalent cycloaliphatic linking group, preferably up to 8 carbon atoms, e.g., cyclohexyl, and the like. However, other divalent linking groups can be used, depending on the technique used to prepare the polymer. For example, if a hydroxyalkyl carbamate is adducted onto an isocyanate-functional acrylic polymer, the linking group L' would include an —NHCOO-urethane linkage as a residue of the isocyanate group.

A most preferred carbamate and hydroxyl functional polymer for use as film-forming component (a) will have a number average molecular weight of from 1000 to 5000, a carbamate equivalent weight of from 300 to 600, and a T$_g$ of from 0 to 150° C. In an especially preferred embodiment, the carbamate-functional polymer will have a number average molecular weight of from 1500 to 3000, a carbamate equivalent weight of from 350 to 500, and a Tg of from 25 to 100° C.

This most preferred carbamate functional polymer for use as film-forming component (a) will have from at least 66 to 100% by weight, based on the total weight of the polymer, of one or more repeat units A selected from the group consisting of

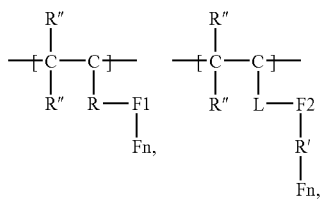

and mixtures thereof, and
from 0 to less than 35% by weight, based on the total weight of the polymer, of one or more repeat units A' having the structure

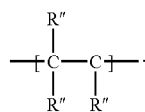

In one exemplary embodiment, the crosslinkable resin be this carbamate functional acrylic resin that has from 80 to 100 weight percent of one or more repeat units A and from 20 to 0 weight percent of one or more repeat units A', and most preferably, from 90 to 100 weight percent of one or more repeat units A and from 10 to 0 weight percent of one or more repeat units A', based on the total weight of the final carbamate functional polymer. A particularly preferred carbamate functional polymer of the invention will have more than 90 weight percent of one or more repeat units A and less than 10 weight percent, preferably between 1 and 9 weight percent, of one or more repeat units A', based on the total weight of the carbamate functional polymer of the invention.

In the above, R is an at least divalent nonfunctional linking group having from 1 to 60 carbon atoms and from 0 to 20 heteroatoms selected from the group consisting of oxygen, nitrogen, sulfur, phosphorus, and silane, and mixtures thereof. As used here, "nonfunctional" refers to the absence of groups that are reactive with crosslinking agents under traditional coating curing conditions.

Illustrative examples of suitable R groups are aliphatic or cycloaliphatic linking groups of from 1 to 60 carbons, aromatic linking groups of from 1 to 10 carbons, and mixtures thereof. Preferred R groups include aliphatic or cycloaliphatic groups of from 2 to 10 carbons. R may, and preferably will, include one or more heteroatoms via one or more divalent internal linking groups such as esters, amides, secondary carbamates, ethers, secondary ureas, ketones, and mixtures thereof. Internal linking groups selected from the group consisting of esters, secondary carbamates, and mixtures thereof, are more preferred, with esters being most preferred.

A most preferred R group is

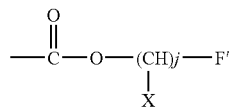

wherein j is from 1 to 6 and X is H or is a monovalent nonfunctional linking group having from 1 to 20 carbon atoms and from 0 to 20 heteroatoms selected from the group consisting of oxygen, nitrogen, sulfur, phosphorus, and silane, and mixtures thereof.

R' is an at least monovalent nonfunctional linking group having from 1 to 60 carbon atoms and from 0 to 20 heteroatoms selected from the group consisting of oxygen, nitrogen, sulfur, phosphorus, and silane, and mixtures thereof. As used here, "nonfunctional" refers to the absence of groups that are reactive with crosslinking agents under traditional coating curing conditions.

Illustrative examples of suitable R' groups are aliphatic or cycloaliphatic linking groups of from 1 to 60 carbons, aromatic linking groups of from 1 to 10 carbons, and mixtures thereof. Preferred R' groups include aliphatic or cycloaliphatic groups of from 2 to 10 carbons. R' may, and preferably will, include one or more heteroatoms via one or more divalent internal linking groups such as esters, amides, secondary carbamates, ethers, secondary ureas, ketones, and mixtures thereof. The use of esters as internal linking groups is most preferred.

Examples of particularly preferred R' groups are

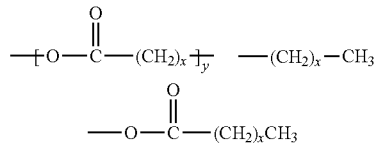

wherein x and y are from 0 to 10, preferably from 3 to 8.

In one exemplary embodiment, the at least monovalent nonfunctional linking group R' will comprise at least one branched alkyl group of from 5 to 20 carbons, preferably from 5 to 15 carbons and most preferably from 8 to 12 carbons. An example of an especially suitable structure for incorporation into linking group R' is

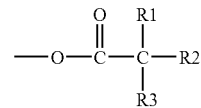

wherein R1, R2, and R3 are alkyl groups of from 1 to 10 carbons each. Most preferably, R1, R2, and R3 will total from 8 to 12 carbons with at least one of R1, R2, and R3 being a methyl group. In a most preferred embodiment, n will be 0 when R' comprises this branched alkyl structure.

R" is H or a monovalent nonfunctional linking group having from 1 to 20 carbon atoms and from 0 to 20 heteroatoms selected from the group consisting of oxygen, nitrogen, sulfur, phosphorus, and silane, and mixtures thereof.

Illustrative examples of suitable R" groups are hydrogen, aliphatic or cycloaliphatic linking groups of from 1 to 60 carbons, aromatic linking groups of from 1 to 10 carbons, and mixtures thereof. R" may, and preferably will, include one or more heteroatoms via one or more divalent internal linking groups such as esters, amides, secondary carbamates, ethers, secondary ureas, ketones, and mixtures thereof.

Preferred R" groups are H, —$CH_3$, aromatic groups such as benzyl, and alkyl esters of from 2 to 10 carbons, especially from 4 to 8 carbons. H and methyl are most preferred as R".

L is an at least trivalent nonfunctional linking group having from 1 to 60 carbon atoms and from 0 to 20 heteroatoms selected from the group consisting of oxygen, nitrogen, sulfur, phosphorus, and silane, and mixtures thereof. As used here, "nonfunctional" refers to the absence of groups that are reactive with crosslinking agents under traditional coating curing conditions.

Illustrative examples of suitable L groups are aliphatic or cycloaliphatic linking groups of from 1 to 60 carbons, aromatic linking groups of from 1 to 10 carbons, and mixtures thereof. Preferred L groups include aliphatic or cycloaliphatic groups of from 2 to 10 carbons. L may, and preferably will, include one or more heteroatoms via one or more divalent internal linking groups such as esters, amides, secondary carbamates, ethers, secondary ureas, ketones, and mixtures thereof. Internal linking groups selected from the group consisting of esters, secondary carbamates, and mixtures thereof, are more preferred, with esters being most preferred.

An example of preferred L groups are

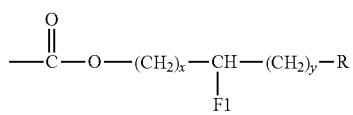

and isomers thereof, wherein F1 and R are as described, x and y may the same or different and are from 0 to 10, preferably from 1 to 3, and is most preferably 1.

F, F1 and F2 are functional groups selected from the group consisting of primary carbamate groups, hydroxyl groups, and mixtures thereof, such as beta-hydroxy primary carbamate groups, with the proviso that at least one of F1 and F2 are a primary carbamate group or a beta-hydroxy primary carbamate group, and n is an integer from 0 to 3, most preferably 0.

Polyesters having active hydrogen groups such as hydroxyl groups can also be used as the crosslinkable resin in the disclosed coating composition. Such polyesters are well-known in the art, and may be prepared by the polyesterification of organic polycarboxylic acids (e.g., phthalic acid, hexahydrophthalic acid, adipic acid, maleic acid) or their anhydrides with organic polyols containing primary or secondary hydroxyl groups (e.g., ethylene glycol, butylene glycol, neopentyl glycol).

Carbamate functional polyesters are also suitable for use as the crosslinkable resin in the disclosed coating compositions. Suitable polyesters can be prepared by the esterification of a polycarboxylic acid or an anhydride thereof with a polyol and/or an epoxide. The polycarboxylic acids used to prepare the polyester consist primarily of monomeric polycarboxylic acids or anhydrides thereof having 2 to 18 carbon atoms per molecule. Among the acids that are useful are phthalic acid, hexahydrophthalic acid, adipic acid, sebacic acid, maleic acid, and other dicarboxylic acids of various types. Minor amounts of monobasic acids can be included in the reaction mixture, for example, benzoic acid, stearic acid, acetic acid, and oleic acid. Also, higher carboxylic acids can be used, for example, trimellitic acid and tricarballylic acid. Anhydrides of the acids referred to above, where they exist, can be used in place of the acid. Also, lower alkyl esters of the acids can be used, for example, dimethyl glutarate and dimethyl terephthalate.

Polyols that can be used to prepare suitable polyesters include diols such as alkylene glycols. Specific examples include ethylene glycol, 1,6-hexanediol, neopentyl glycol, and 2,2-dimethyl-3-hydroxypropyl-2,2-dimethyl-3-hydroxypropionate. Other suitable glycols include hydrogenated bisphenol A, cyclohexanediol, cyclohexanedimethanol, caprolactone-based diols such as the reaction product of e-caprolactone and ethylene glycol, hydroxy-alkylated bisphenols, polyether glycols such as poly(oxytetramethylene)glycol, and the like.

Although the polyol component can comprise all diols, polyols of higher functionality can also be used. It is preferred that the polyol be a mixture of at least one diol and at least one triol, or one polyol of higher functionality. Examples of polyols of higher functionality would include trimethylol ethane, trimethylol propane, pentaerythritol, and the like. Triols are preferred. The mole ratio of polyols of higher functionality to diol is generally less than 3.3/1, preferably up to 1.4/1.

Carbamate groups can be incorporated into the polyester by first forming a hydroxyalkyl carbamate that can be reacted with the polyacids and polyols used in forming the polyester. A polyester oligomer can be prepared by reacting a polycarboxylic acid such as those mentioned above with a hydroxyalkyl carbamate. An example of a hydroxyalkyl carbamate is the reaction product of ammonia and propylene carbonate. The hydroxyalkyl carbamate is condensed with acid functionality on the polyester or polycarboxylic acid, yielding terminal carbamate functionality. Terminal carbamate functional groups can also be incorporated into the polyester by reacting isocyanic acid with a hydroxy functional polyester. Also, carbamate functionality can be incorporated into the polyester by reacting a hydroxy functional polyester with urea.

Carbamate groups can also be incorporated into the polyester by a transcarbamalation reaction. In this reaction, a low molecular weight carbamate functional material derived from a low molecular weight alcohol or glycol ether such as methyl carbamate is reacted with the hydroxyl groups of a hydroxyl functional polyester, yielding a carbamate functional polyester and the original alcohol or glycol ether. The low molecular weight carbamate functional material derived from an alcohol or glycol ether is first prepared by reacting the alcohol or glycol ether with urea in the presence of a catalyst. Suitable alcohols include lower molecular weight aliphatic, cycloaliphatic, and aromatic alcohols such as methanol, ethanol, propanol, butanol, cyclohexanol, 2-ethylhexanol, and 3-methylbutanol. Suitable glycol ethers include ethylene glycol methyl ether and propylene glycol methyl ether. Propylene glycol methyl ether is preferred.

Besides carbamate functionality, polyester polymers and oligomers suitable for use as the crosslinkable resin may contain other functional groups such as hydroxyl, carboxylic acid and/or anhydride groups. The equivalent weight of such polyesters containing terminal carbamate groups may be from about 140 to 2500, based on equivalents of carbamate groups. The equivalent weight is a calculated value based on the relative amounts of the various ingredients used in making the polyester, and is based on the solids of the material.

Polyurethanes having active hydrogen functional groups such as described above which are suitable for use as the crosslinkable resin are also well known in the art. They are prepared by a chain extension reaction of a polyisocyanate (e.g., hexamethylene diisocyanate, isophorone diisocyanate, MDI, etc.) and a polyol (e.g., 1,6-hexanediol, 1,4-butanediol, neopentyl glycol, trimethylol propane). They can be provided with active hydrogen functional groups by capping the polyurethane chain with an excess of diol, polyamine, amino alcohol, or the like.

Carbamate functional polyurethanes may be prepared by reacting the active hydrogen groups with a low molecular weight carbamate functional material derived from a low molecular weight alcohol or glycol ether such as methyl.

Other carbamate functional compounds preferred for use as a crosslinkable resin are carbamate-functional compounds which are the reaction product of a mixture comprising a polyisocyanate or a chain extended polymer, and a compound comprising a group that is reactive with isocyanate or a functional group on the chain extended polymer as well as a carbamate group or group that can be converted to carbamate. Such compounds are described in U.S. Pat. Nos. 5,373,069 and 5,512,639 hereby incorporated by reference.

In one exemplary embodiment, the crosslinkable resin may be at least one of carbamate functional acrylics, carbamate functional modified acrylics, hydroxyl functional acrylics, hydroxyl functional modified acrylics, polyurethanes, polyesters and mixtures thereof, with carbamate functional acrylics, hydroxyl functional acrylics, and carbamate/hydroxyl functional acrylics as described above being used in one particularly exemplary embodiment In one exemplary embodiment, the film-forming component will also comprise a crosslinking agent. For example, generally known crosslinking agents can be incorporated in a composition of the invention particularly when the crosslinkable resin comprises a thermosetting resin containing active hydrogen or amino functionality.

As will be appreciated by one skilled in the art, the choice of crosslinking agent depends on various factors such as compatibility with the film-forming resin, the particular type of functional groups on the film-forming resin and the like. The crosslinking agent is used to crosslink the film-forming resin by either condensation reactions or non-free radical addition reactions or a combination of both of these. When for example the thermosetting reactants can be crosslinked in the presence of moisture or when the reactants include monomers having complementary groups capable of entering into crosslinking reactions, the crosslinking agent may be omitted if desired.

Representative examples of crosslinking agents include blocked and/or unblocked diisocyanates, diepoxides, aminoplasts, phenol/formaldehyde adducts, carbamates, siloxane groups, cyclic carbonate groups, and anhydride groups. Examples of such compounds include melamine formaldehyde resin (including monomeric or polymeric melamine resin and partially or fully alkylated melamine resin), urea resins (e.g., methylol ureas such as urea formaldehyde resin, alkoxy ureas such as butylated urea formaldehyde resin), polyanhydrides (e.g., polysuccinic anhydride), and polysiloxanes (e.g., trimethoxy siloxane). Aminoplast resin such as melamine formaldehyde resin or urea formaldehyde resin are especially preferred. Even more preferred are aminoplast resins where one or more of the amino nitrogens is substituted with a carbamate group. When aminoplast resins are employed as the crosslinking agent, particularly suitable are the melamine-formaldehyde condensates in which a substantial proportion of the methylol groups have been etherified by reaction with a monohydric alcohol.

In preferred embodiments, the crosslinking agent is at least about 5%, more preferably at least about 10% by weight of the nonvolatile vehicle. "Nonvolatile vehicle" refers to the film-forming components. It is also preferred for the crosslinking agent to be up to about 40%, more preferably up to about 30% by weight of the nonvolatile vehicle. The crosslinking agent is preferably from about 5% to about 40%, more preferably from about 10% to about 35%, and still more preferably from about 15% to about 35% by weight of the nonvolatile vehicle.

It will be appreciated that the disclosed functional silicas, especially the primary carbamate functional silicas may be reactive with the crosslinking agent. Accordingly, in one exemplary embodiment, when the functional silica is a primary carbamate functional silica, the crosslinking agent will be an aminoplast resin.

The disclosed coating compositions may further include a catalyst to enhance the cure reaction. For example, when aminoplast compounds, especially monomeric melamines, are used as a curing agent, a strong acid catalyst may be utilized to enhance the cure reaction. Such catalysts are well-known in the art and include, without limitation, p-toluene sulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

A solvent or solvents may be utilized in the coating composition. In general, the solvent can be any organic solvent and/or water. In one preferred embodiment, the solvent includes a polar organic solvent. More preferably, the solvent includes one or more organic solvents selected from polar aliphatic solvents or polar aromatic solvents. Still more preferably, the solvent includes a ketone, ester, acetate, aprotic amide, aprotic sulfoxide, aprotic amine, or a combination of any of these. Examples of useful solvents include, without limitation, methyl ethyl ketone, methyl isobutyl ketone, m-amyl acetate, ethylene glycol butyl ether-acetate, propylene glycol monomethyl ether acetate, xylene, N-methylpyrrolidone, blends of aromatic hydrocarbons, and mixtures of these. In another preferred embodiment, the solvent is water or a mixture of water with small amounts of co-solvents.

In one embodiment, the disclosed coating composition may be a powder coating or powder slurry coating.

When the coating composition is a primer composition or pigmented topcoat composition, such as a basecoat composition, one or more pigments and/or fillers may be included. Pigments and fillers may be utilized in amounts typically of up to 40% by weight, based on total weight of the coating composition. The pigments used may be inorganic pigments, including metal oxides, chromates, molybdate, phosphates, and silicates. Examples of inorganic pigments and fillers that could be employed are titanium dioxide, barium sulfate, carbon black, ocher, sienna, umber, hematite, limonite, red iron oxide, transparent red iron oxide, black iron oxide, brown iron oxide, chromium oxide green, strontium chromate, zinc phosphate, silicas such as fumed silica, calcium carbonate, talc, barytes, ferric ammonium ferrocyanide (Prussian blue), ultramarine, lead chromate, lead molybdate, and mica flake pigments. Organic pigments may also be used. Examples of useful organic pigments are metallized and non-metallized azo reds, quinacridone reds and violets, perylene reds, copper phthalocyanine blues and greens, carbazole violet, monoarylide and diarylide yellows, benzimidazolone yellows, tolyl orange, naphthol orange, and the like.

Additional agents, for example hindered amine light stabilizers, ultraviolet light absorbers, anti-oxidants, surfactants, stabilizers, wetting agents, rheology control agents, dispersing agents, adhesion promoters, etc. may be incorporated into the coating composition. Such additives are well known and may be included in amounts typically used for coating compositions.

Coating compositions can be coated on the article by any of a number of techniques well known in the art. These include, for example, spray coating, dip coating, roll coating, curtain coating, and the like. For automotive body panels, spray coating is preferred.

The coating composition can be applied onto many different substrates, including metal substrates such as bare steel, phosphated steel, galvanized steel, or aluminum; and non-metallic substrates, such as plastics and composites. The substrate may also be any of these materials having upon it already a layer of another coating, such as a layer of an electrodeposited primer, primer surfacer, and/or basecoat, cured or uncured.

Application can be, for example, by electrostatic spraying or by use of a fluidized bed. Electrostatic spraying is the preferred method. The coating composition can be applied in one or more passes to provide a film thickness after cure of typically from about 20 to about 100 microns.

After application of the coating composition to the substrate, the coating is cured, preferably by heating at a temperature and for a length of time sufficient to cause the reactants to form an insoluble polymeric network. The cure temperature is usually from about 105° C. to about 175° C., and the length of cure is usually about 15 minutes to about 60 minutes. Preferably, the coating is cured at about 120° C. to about 150° C. for about 20 to about 30 minutes. Heating can be done in infrared and/or convection ovens.

The coating composition is preferably utilized as the clearcoat of an automotive composite color-plus-clear coating. The pigmented basecoat composition over which it is applied may any of a number of types well-known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of crosslinkable functional groups. Such groups include, for example, hydroxy, isocyanate, amine, epoxy, acrylate, vinyl, silane, and acetoacetate groups. These groups may be masked or blocked in such a way so that they are unblocked and available for the crosslinking reaction under the desired curing conditions, generally elevated temperatures. Useful crosslinkable functional groups include hydroxy, epoxy, acid, anhydride, silane, and acetoacetate groups. Preferred crosslinkable functional groups include hydroxy functional groups and amino functional groups.

Basecoat polymers may be self-crosslinkable, or may require a separate crosslinking agent that is reactive with the functional groups of the polymer. When the polymer comprises hydroxy functional groups, for example, the crosslinking agent may be an aminoplast resin, isocyanate and blocked isocyanates (including isocyanurates), and acid or anhydride functional crosslinking agents.

The clearcoat coating composition is generally applied wet-on-wet over a basecoat coating composition as is widely done in the industry. The coating compositions described herein are preferably subjected to conditions so as to cure the coating layers. Although various methods of curing may be used, heat-curing is preferred. Generally, heat curing is effected by exposing the coated article to elevated temperatures provided primarily by radiative heat sources. Curing temperatures will vary depending on the particular blocking groups used in the crosslinking agents, however they generally range between 90° C. and 180° C. In a preferred embodiment, the cure temperature is preferably between 115° C. and 150° C., and more preferably at temperatures between 115° C. and 140° C. for a blocked acid catalyzed system. For an unblocked acid catalyzed system, the cure temperature is preferably between 80° C. and 100° C. The curing time will vary depending on the particular components used, and physical parameters such as the thickness of the layers; however, typical curing times range from 15 to 60 minutes, and preferably 15-25 minutes for blocked acid catalyzed systems and 10-20 minutes for unblocked acid catalyzed systems. The curing times may also be expressed as time after metal temperature reaches the bake temperature ("metal temperature"). For example, the curing time may be for 5 to 30 minutes, preferably 10 to 20 minutes, at metal temperature.

The disclosed method is advantageous in that the disclosed functional silicas, especially the carbamate functional silicas, provide improvements in durability, water resistance, chemical resistance, scratch and mar resistance, etch resistance, humidity resistance, and/or overall appearance of coating compositions incorporating such functional silicas. The functional silicas are also advantageous in that they are believed to be non-toxic.

EXAMPLE

With a Nitrogen bubbler running, a stirred mixture of 1000 parts xylene, 200 parts of Cab-o-sil™ from Cavot Corperation that is pre-dried in a 110° C. oven for four days, and 40 parts of urea are heated in a reactor to 135° C. The gasses from the reaction (Nitrogen from the bubbler and ammonia from the decomposition of urea) are collected in a water trap. The reaction is followed measuring the amount of ammonia produced. Once the reaction is complete, the reaction mixture is filtered to give carbamated silica.

The invention claimed is:

1. A carbamate functional silica, comprising repeating units of the structure:

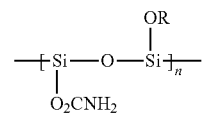

wherein R is H or a hydrocarbon of from 1 to 50 carbon atoms and n is a number from 2 to 100.

2. The carbamate functional silica of claim 1 wherein the repeating units are on the surface of primary particles of fumed silica.

3. A curable coating comprising the carbamate functional silica of claim 1.

4. The curable coating composition of claim 3 further comprising a film-forming component.

5. The curable coating composition of claim 4 wherein the film-forming component comprises an aminoplast crosslinking agent.

6. The curable coating composition of claim 5 wherein the carbamate functional silica is reactive with the aminoplast crosslinking agent.

7. The curable coating composition of claim 4 wherein the film-forming component comprises an active hydrogen compound that is at least one of a carbamate functional polymer, a hydroxyl functional polymer, or a combination thereof.

8. A method of making a carbamate functional silica, comprising
providing a fumed silica having a plurality of silanol groups, reacting one or more of the silanol groups with at least one of (i) ammonia and hydrogencyanate; (ii) an alkyl carbamate in the presence of a tin catalyst; or (iii) phosgene and ammonia to provide a carbamate functional silica of the structure:

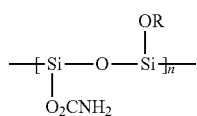

wherein R is an alkyl group of from 1 to 50 carbon atoms and n is a number from 2 to 100.

9. A functional silica comprising repeating units of the structure:

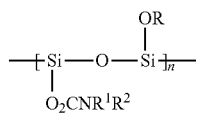

wherein R is H or a hydrocarbon group of from 1 to 50 carbon atoms, n is a number from 2 to 100, $R^1$ and $R^2$ may be the same or different and are at least one of a hydrocarbon group comprising from 1 to 100 carbon atoms with the provisos that at least one of $R^1$ and $R^2$ is not hydrogen and at least one of $R^1$ and $R^2$ comprises at least one functional group that is an ester, an ether, an amine group, a heterocyclic group, or a mixture thereof.

10. A functional silica comprising repeating units of at least one of structure (I) or (II):

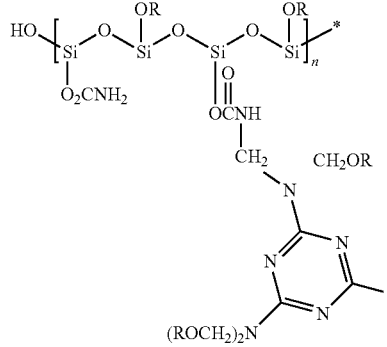

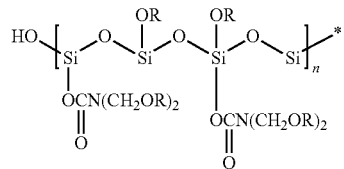

wherein R is H or a hydrocarbon of from 1 to 50 carbon atoms, n is a number from 2 to 100, and R' is —$(CH_2)_x$ $CH_3$ wherein x is a number from 0 to 3.

* * * * *